(12) United States Patent
Uang et al.

(10) Patent No.: US 8,865,893 B2
(45) Date of Patent: Oct. 21, 2014

(54) METHOD FOR PREPARING 2-MORPHOLINOISOBORNANE-10-THIOL AND INTERMEDIATES FORMED THEREIN

(75) Inventors: Biing-Jiun Uang, Hsinchu (TW); Yu-Han Tsao, Hsinchu (TW); Ping-Yu Wu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 449 days.

(21) Appl. No.: 12/901,117

(22) Filed: Oct. 8, 2010

(65) Prior Publication Data

US 2011/0269955 A1     Nov. 3, 2011

(30) Foreign Application Priority Data

Apr. 30, 2010 (TW) ................................ 99113827 A

(51) Int. Cl.
| | | |
|---|---|---|
| *C07D 265/30* | (2006.01) | |
| *C07C 311/10* | (2006.01) | |
| *C07D 295/26* | (2006.01) | |
| *C07C 323/26* | (2006.01) | |
| *C07D 295/096* | (2006.01) | |

(52) U.S. Cl.
CPC .......... *C07D 295/096* (2013.01); *C07C 311/10* (2013.01); *C07C 2102/42* (2013.01); *C07D 295/26* (2013.01); *C07C 323/26* (2013.01)

USPC ......................................................... 544/106

(58) Field of Classification Search
USPC ........................... 564/267, 462; 544/158, 159
See application file for complete search history.

(56) References Cited

U.S. PATENT DOCUMENTS 7,485,755 B2 *   2/2009  Suzuki et al. .................. 564/462
2004/0266732 A1 * 12/2004 Galvez et al. ................... 514/79

OTHER PUBLICATIONS

Kozakiewicz (J Mol. Cat. (available online May 11, 2010) 326:128).*
(Cremlyn et al, "Amphor- and 10-sulfonamidocamphor sulfonhydrazones and related compounds" Phosphorus and Sulfur and the Related Elements (1988), 40(1-2), 91-7).*
Database Caplus Chemical Abstracts Service, Columbus, Ohio, US; Database Accession No. 1992:511092, Abstract of Oppolzer et al., Journal of the American Chemical Society (1992), 114(14), 5900-2.*
Database Caplus Chemical Abstracts Service, Columbus, Ohio, US; Database Accession No. 2004:522646, Abstract of Gayet et al., Organic & Biomolecular Chemistry (2004), 2(13), 1887-1893.*

* cited by examiner

*Primary Examiner* — Karl J Puttlitz
(74) *Attorney, Agent, or Firm* — Muncy, Geissler, Olds & Lowe, P.C.

(57) ABSTRACT

A method for preparing 2-morpholinoisobornane-10-thiol is disclosed, which has simplified steps and avoids the use of Na metal. Accordingly, it is advantageous to apply the method in a mass production.

19 Claims, No Drawings

METHOD FOR PREPARING 2-MORPHOLINOISOBORNANE-10-THIOL AND INTERMEDIATES FORMED THEREIN

BACKGROUND OF THE INVENTION

1. Field of the Invention

The present invention relates to a method for preparing 2-morpholinoisobornane-10-thiol and intermediates formed therein.

2. Description of Related Art

Generally, an enzyme has its specific structural conformation in bioorganisms. In enzymatic catalysis, the enzyme can only recognize and catalyze particular enantiomers having the recognizable chirality among various enantiomers having different chirality. Therefore, catalytic asymmetric carbon-carbon bond forming reactions are very important in order to synthesize pharmaceutical compounds or natural products that are active in enzymatic catalysis.

Enantioselective addition of organozincs to carbonyl compounds, one of the most powerful methods for constructing chiral carbon-carbon bonds, has been widely studied. In the endeavors of the study, a camphor-derived chiral ligand has been developed for the use in catalytic asymmetric reactions, and that is (−)-2-exo-morpholinoisobornane-10-thiol ((−)-MITH). (−)-MITH can be applied in asymmetric reaction for forming chiral carbon-carbon bonds, for example, reactions shown in the following Schemes 1 and 2.

Scheme 1

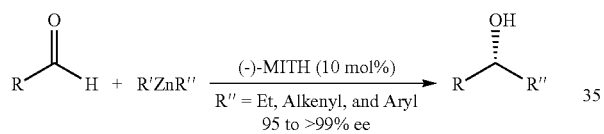

Scheme 2

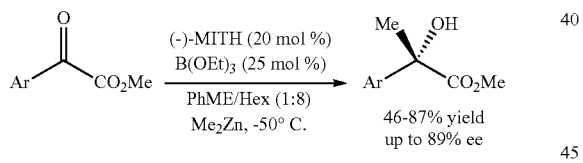

According to the abovementioned schemes, diarylmethanol derivatives can be prepared. For example, chiral diarylmethanol intermediates used in preparation of pharmaceutical compounds like CDP840 and its analogues for the treatment of asthma and chronic obstructive pulmonary disease, orphenadrine, neobenodine, carbinoxamine, and so on, all can be synthesized in a reaction with (−)-MITH as a chiral ligand.

A known method for preparing (−)-MITH accords to the following Scheme 3.

Scheme 3

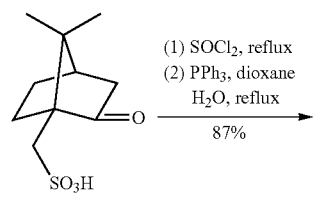

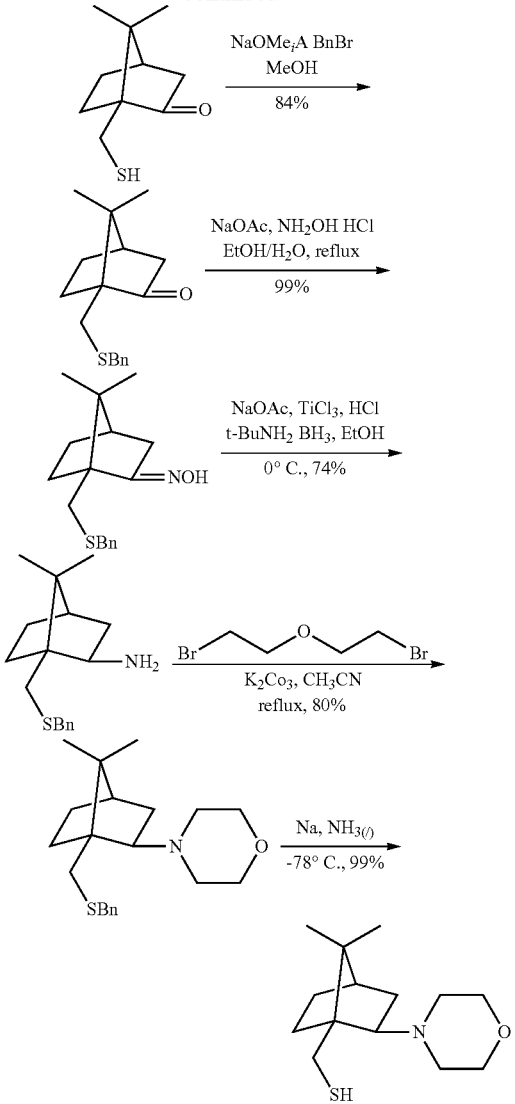

First, the sulfonic acid group in (1S)-(+)-camphorsulfonic acid is reduced into mercapto and then protected with BnBr. The subsequent steps including formation of oxime, reduction to form amine, formation of morpholino, and final use of sodium to remove Bn from S to form mercapto, are necessary to be carried out. Accordingly, the preparation of (−)-MITH contains six steps in total. However, since the final step in the preparation is the use of sodium, this method is dangerous and disadvantageous in mass production.

SUMMARY OF THE INVENTION

In view of the abovementioned, an object of the present invention is to provide a method for preparing 2-morpholinoisobornane-10-thiol. The method is constructed by simplified steps which do not include the use of sodium, and therefore, 2-morpholinoisobornane-10-thiol can be prepared easily and safely.

In order to achieve the object depicted above, one aspect of the present invention provides a method for preparing 2-morpholinoisobornane-10-thiol, comprising the following steps: (a) providing a compound represented by formula (I),

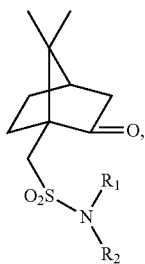
(I)

wherein each of $R_1$ and $R_2$, independently, is $C_{1-6}$ alkyl, $C_{5-10}$ cycloalkyl, $C_{4-9}$ heterocycloalkyl, $C_{6-10}$ aryl, or $C_{5-9}$ heteroaryl, and the heterocycloalkyl and the heteroaryl have at least one heteroatom selected from the group consisting of oxygen, sulfur, and nitrogen, or $R_1$ and $R_2$ together form $-(CH_2)_xZ(CH_2)_y-$, wherein x and y is 1, 2, or 3, and Z is $CH_2$, NH, O, or S;

(b) converting the compound represented by formula (I) into a compound represented by formula (II),

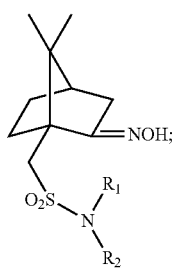
(II)

(c) reducing the compound represented by formula (II) into a compound represented by formula (III),

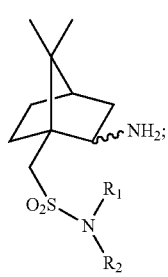
(III)

(d) forming a compound represented by formula (IV),

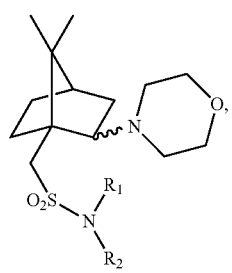
(IV)

by N-alkylation of the compound represented by formula (III) with $W_1-(CH_2)_2O(CH_2)_2-W_2$, wherein $W_1$ and $W_2$ are leaving groups; and (e) reducing the compound represented by formula (IV) into 2-morpholinoisobornane-10-thiol.

In the method mentioned above, the compound represented by formula (I) in step (a) is formed by sulfamidation of (1S)-(+)-camphorsulfonic acid with a compound represented by formula (V),

(V)

In the method mentioned above, hydroxylamine can be used as an iminating agent in step (b); t-$BuNH_2 \cdot BH_3$ can be used as a reductant in step (c); the leaving groups in step (d) can be halogen or sulfonate; and $LiAlH_4$ can be used as a reductant in step (e).

Besides, another aspect of the present invention provides a method for preparing 2-morpholinoisobornane-10-thiol, comprising the following steps: (a) providing a compound represented by formula (IV),

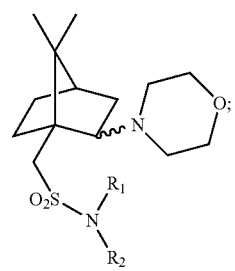
(IV)

wherein each of $R_1$ and $R_2$, independently, is $C_{1-6}$ alkyl, $C_{5-10}$ cycloalkyl, $C_{4-9}$ heterocycloalkyl, $C_{6-10}$ aryl, or $C_{5-9}$ heteroaryl, and the heterocycloalkyl and the heteroaryl have at least one heteroatom selected from the group consisting of oxygen, sulfur, and nitrogen, or $R_1$ and $R_2$ together form $-(CH_2)_xZ(CH_2)_y-$, wherein x and y is 1, 2, or 3, and Z is $CH_2$, NH, O, or S; and (b) reducing the compound represented by formula (IV) into 2-morpholinoisobornane-10-thiol.

In the method described above, $LiAlH_4$ can be used as a reductant in step (b); the compound represented by formula (IV) is formed by N-alkylation of a compound represented by formula (III) with $W_1-(CH_2)_2O(CH_2)_2-W_2$,

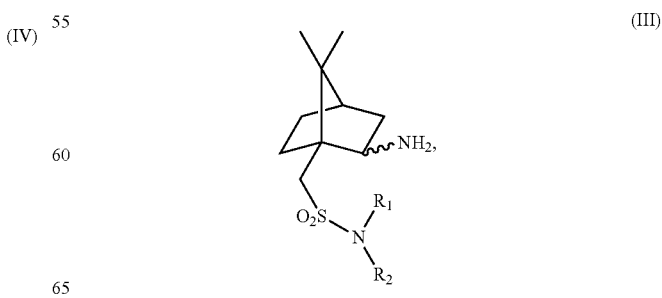
(III)

wherein $W_1$ and $W_2$ are leaving groups.

The leaving groups mentioned above can be diazonium salt, halogen, sulfonate, nitrate, phosphate, tetraalkylammonium salt, ester, and so on. Specially, —N$_2$$^+$, —OR'$_2$$^+$, —OSO$_2$C$_4$F$_9$, —OSO$_2$CF$_3$, —OSO$_2$F, —OTs, —OMs, —I$^-$, —Br$^-$, —OH$_2$$^+$, —Cl$^-$, —OHR'$^+$, —ONO$_2$, —OPO(OH)$_2$, —SR'$_2$$^+$, —NR'$_3$$^+$, —F$^-$, and —OCOR' where R' may be alkyl or aryl are some examples.

In the abovementioned method of the present invention, (-)-2-exo-morpholinoisobornane-10-thiol or (-)-2-endo-morpholinoisobornane-10-thiol may be prepared alone. Alternatively, racemic mixture of 2-morpholinoisobornane-10-thiol or chiral mixture thereof (having optical activity) may be prepared.

The aforesaid compound represented by formula (III) can be formed from imination reaction of a compound represented by formula (II),

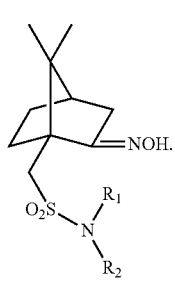

(II)

t-BuNH$_2$.BH$_3$ can be used as a reductant to reduce the compound represented by formula (II) into the compound represented by formula (III).

The compound of formula (II) can be formed by reduction of a compound represented by formula (I),

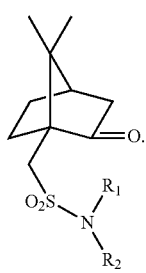

(I)

Hydroxylamine can be used as an iminating agent to convert the compound represented by formula (I) into the compound represented by formula (II).

The abovementioned compound represented by formula (I) can be formed by sulfamidation of (1S)-(+)-camphorsulfonic acid with a compound represented by formula (V),

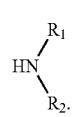

(V)

Referring to the compound represented by formula (V), dimethylamine, methylethylamine, methylpropylamine, propylhexylamine, diphenylamine, pyrrolidine, oxazolidine, isoxazolidine, piperidine, morpholine, thiazolidine, and isothiazolidine can be exemplified.

Furthermore, still another aspect of the present invention provides a compound represented by formula (VI):

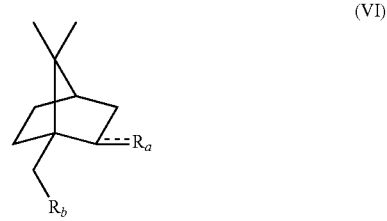

(VI)

wherein ═ is a single or double bond, R$_a$ is amino, morpholino, O, or NOH, and R$_b$ is SH or

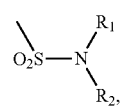

wherein each of R$_1$ and R$_2$, independently, is C$_{1-6}$ alkyl, C$_{5-10}$ cycloalkyl, C$_{4-9}$ heterocycloalkyl, C$_{6-10}$ aryl, or C$_{5-9}$ heteroaryl, and the heterocycloalkyl and the heteroaryl have at least one heteroatom selected from the group consisting of oxygen, sulfur, and nitrogen, or R$_1$ and R$_2$ together form —(CH$_2$)$_x$Z(CH$_2$)$_y$—, wherein x and y is 1, 2, or 3, and Z is CH$_2$, NH, O, or S; with a proviso that, when ═ is a single bond, R$_a$ is amino or morpholino; when ═ is a double bond, R$_a$ is O or NOH; and when R$_b$ is SH, ═ is an endo single bond and R$_a$ is morpholino.

The compounds of the aforesaid aspect can be prepared by the method of the present invention. In one subgroup of the compounds, x and y are 2, Z is O, and R$_a$ is amino or morpholino; and in another subgroup, x and y are 2, Z is O, and R$_a$ is O or NOH.

Other objects, advantages, and novel features of the invention will become more apparent from the following detailed description when taken in conjunction with the accompanying drawings.

BRIEF DESCRIPTION OF THE DRAWINGS

None.

DETAILED DESCRIPTION OF THE PREFERRED EMBODIMENT

The method for preparing 2-morpholinoisobornane-10-thiol in the present invention accords to the following scheme 4.

Scheme 4

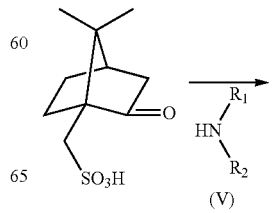

(V)

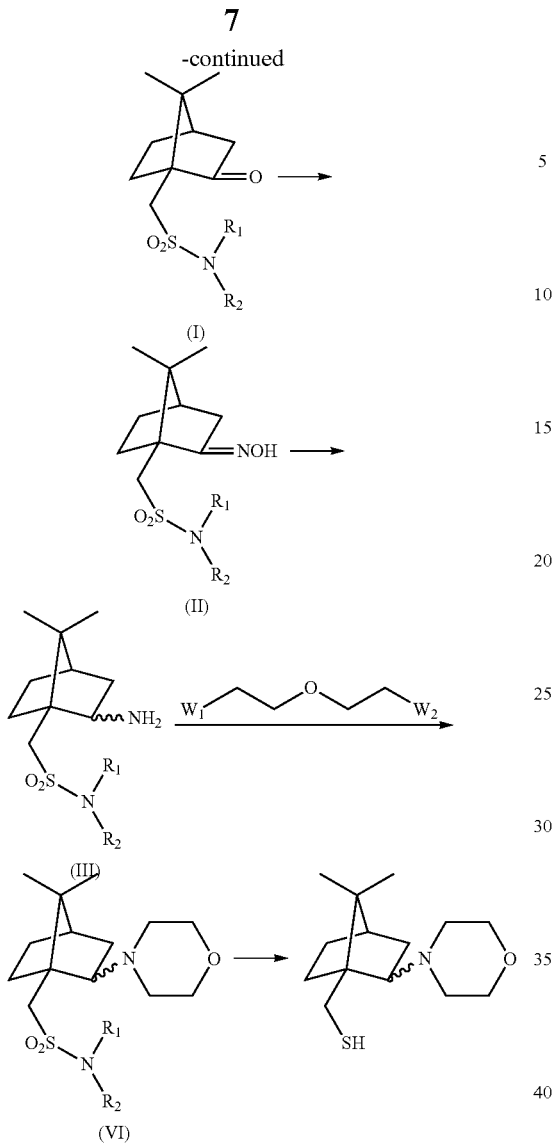

First, (1S)-(+)-camphorsulfonic acid used as a starting material is reacted with a secondary amine represented by formula (V). In the reaction, the sulfonic acid group of (1S)-(+)-camphorsulfonic acid is protected against undesirable reaction in the subsequent steps, and thus a compound represented by formula (I) having sulfonamido is formed.

Subsequently, the compound represented by formula (I) is converted into an oxime represented by formula (II), followed by being directly reduced into a primary amine represented by formula (III). The primary amine represented by formula (III) is N-alkylated with $W_1(CH_2)_2O(CH_2)_2W_2$ to form a compound represented by formula (VI). Finally, the sulfonamide of the compound represented by formula (VI) is reduced into mercapto, and 2-morpholinoisobornane-10-thiol is thus prepared.

The secondary amine represented by formula (V) mentioned above can be replaced by a compound represented by formula (VII) in which x and y is 1, 2, or 3, and Z is CH2, NH, O, or S.

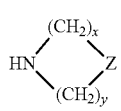

(VII)

For example, pyrrolidine, oxazolidine, isoxazolidine, piperidine, morpholine, thiazolidine, isothiazolidine, and so on may be used as the compound represented by formula (VII) but the present invention is not be limited thereto.

Because of the specific embodiments illustrating the practice of the present invention, a person having ordinary skill in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

Example 1

With reference to the following scheme 5, the preparation of (−)-2-exo-morpholinoisobornane-10-thiol is shown.

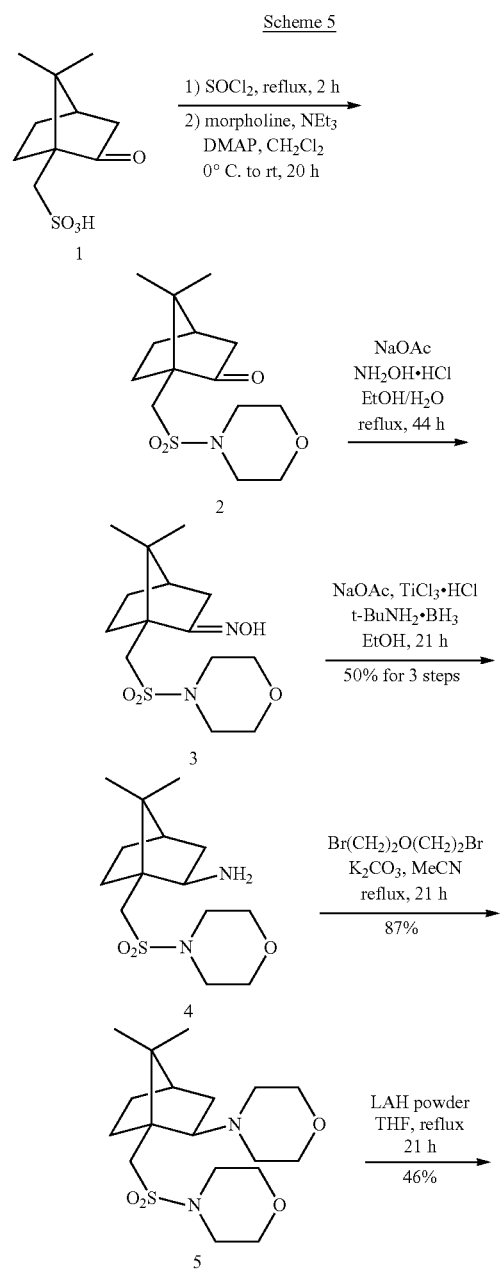

9
-continued

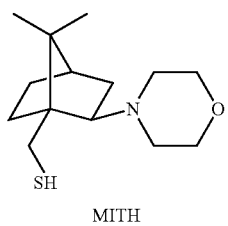

MITH (i) Synthesis of Compound 2

Scheme 5a

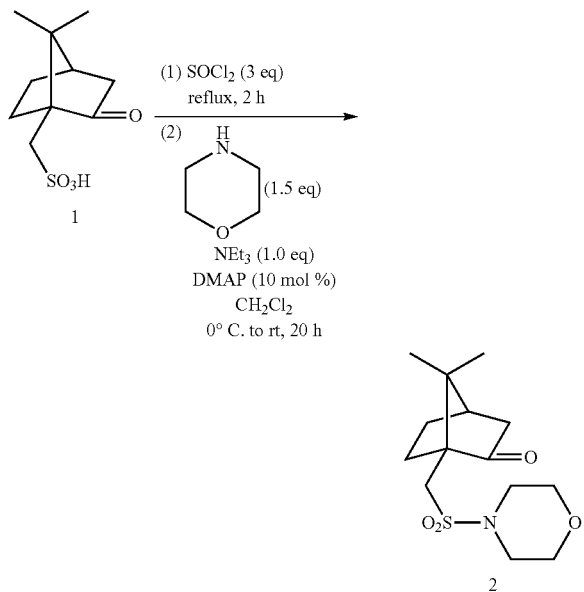

With reference to the scheme 5a, compound 1 (10.02 g, 43.1 mmol) and $SOCl_2$ (10 mL, 137 mmol) were refluxed for 2 hours in a 50-mL round-bottom flask, and then recrystallized in iced n-hexane (100-mL) after being cooled to room temperature. Posterior to filtration, bright white slice solids were obtained. The solids were dissolved in dichloromethane (10 mL), and then slowly dropped into a 100-mL round-bottom flask containing 4-(N,N-dimethylamino)pyridine (DMAP, 0.53 g, 4.3 mmol), dichloromethane (20 mL), morpholine (5.6 mL, 64.7 mmol), and $NEt_3$ (4.4 mL, 43.1 mmol), followed by being stirred at 0° C. for 17 hours then warm to room temperature for additional 3 hours. 1 N HCl aqueous solution was added for neutralization to stop reaction. Water phase was further extracted with dichloromethane (3×20 mL) and then organic phase was collected, dried with anhydrous sodium sulfate, filtrated, and concentrated. The crude extract was purified by column chromatography (gradient elution, ethyl acetate:n-hexane:dichloromethane=1:1:1 to 1:0.25:1 as an eluent) to afford white solid compound 2 (9.77 g, 72%), (7,7-dimethyl-1-(morpholine-4-sulfonylmethyl)-bicyclo [2.2.1]heptan-2-one). The related properties of the compound 2 are listed as follows:

Specific rotation: $[\alpha]_D^{24}$+33.6 (c 1.0, $CHCl_3$).

$^1$H NMR (400 MHz, $CDCl_3$): δ 3.75 (t, J=4.6 Hz, 4H), 3.32 (d, J=14.4 Hz, 1H), 3.30-3.24 (m, 4H), 2.72 (d, J=14.4 Hz, 1H), 2.54-2.46 (m, 1H), 2.37 (dt, J=18.4 Hz, 4.4 Hz, 1H), 2.09 (t, J=4.4 Hz, 1H), 2.07-1.98 (m, 1H), 1.93 (d, J=18.4 Hz, 1H), 1.66-1.59 (m, 1H), 1.45-1.38 (m, 1H), 1.11 (s, 3H), 0.86 (s, 3H).

$^{13}$C NMR (100 MHz, $CDCl_3$): δ 214.9 (C=O), 66.3 ($CH_2$×2), 57.9 (C), 47.7 (C), 45.6 ($CH_2$×2), 44.2 ($CH_2$), 42.5 (CH), 42.3 ($CH_2$), 26.7 ($CH_2$), 24.9 ($CH_2$), 19.7 ($CH_3$), 19.5 ($CH_3$).

10

IR: (neat) 2953, 2890, 2855, 1746, 1343, 1330, 1261, 1151, 1110.

HRMS: calculated for $C_{14}H_{23}NO_4S$ 301.1348. found 301.1335.

(ii) Synthesis of Compound 3

Scheme 5b

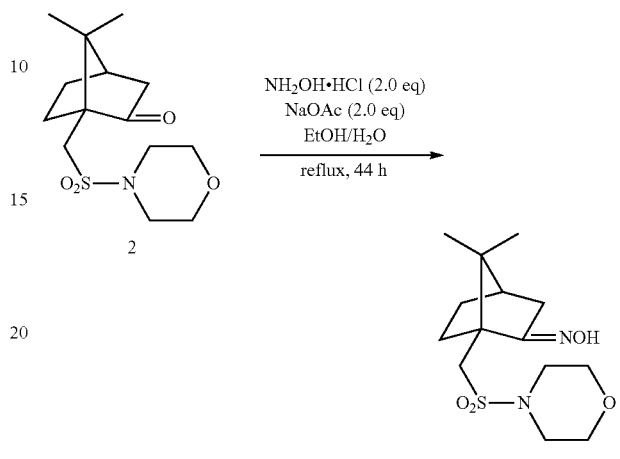

With reference to the Scheme 5b, compound 2 (4.43 g, 14.7 mmol), sodium acetate (2.41 g, 29.4 mmol), $NH_2OH \cdot HCl$ (2.04 g, 29.4 mmol), ethanol (49 mL), and deionized water (24.5 mL) were refluxed for 44 hours in a 250-mL round-bottom flask, and then cooled to room temperature. The mixture was concentrated to remove ethanol. The residual water phase was extracted with dichloromethane (3×30 mL), and then organic phase was collected, dried with anhydrous sodium sulfate, filtrated, and concentrated. The crude extract was purified by column chromatography (gradient elution, ethyl acetate:n-hexane:dichloromethane=1:1:1 to 1:0.25:1 as an eluent) to afford white solid compound 3 (4.51 g, 97%), (7,7-dimethyl-1-(morpholine-4-sulfonylmethyl)-bicyclo [2.2.1]heptan-2-one oxime). The related properties of the compound 3 are listed as follows:

Specific rotation: $[\alpha]_D^{24}$−20.8 (c 1.1, $CHCl_3$).

$^1$H NMR (400 MHz, $CDCl_3$) δ 7.58 (br, 1H), 3.75 (t, J=4.8 Hz, 4H), 3.37 (d, J=14.4 Hz, 1H), 3.32-3.20 (m, 4H), 2.85 (d, J=14.4 Hz, 1H), 2.55 (dt, J=18.0 Hz, 4.0 Hz, 1H), 2.48-2.38 (m, 1H), 2.05 (d, J=17.6 Hz, 1H), 1.98-1.84 (m, 2H), 1.78-1.66 (m, 1H), 1.36-1.26 (m, 1H), 1.04 (s, 3H), 0.82 (s, 3H).

$^{13}$C NMR (100 MHz, $CDCl_3$) δ 167.3 (C=N), 66.5 ($CH_2$×2), 51.9 (C), 50.0 (C), 46.4 ($CH_2$), 45.7 ($CH_2$×2), 43.2 (CH), 32.8 ($CH_2$), 28.1 ($CH_2$), 27.1 ($CH_2$), 19.3 ($CH_3$), 19.1 ($CH_3$).

IR (neat) 3336, 2953, 2920, 2853, 1456, 1343, 1331, 1156, 1113.

(iii) Synthesis of Compounds 4 and 4a

Scheme 5c

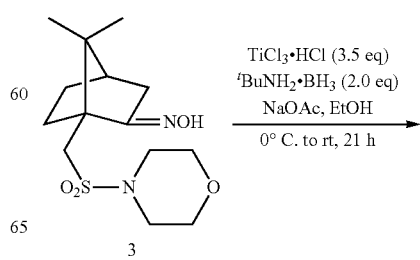

-continued

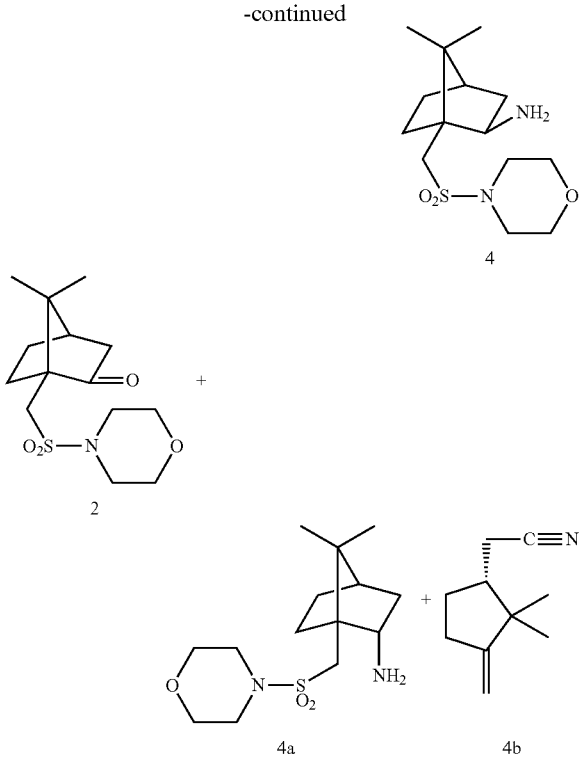

With reference to the Scheme 5c, sodium acetate (0.72 g, 8.8 mmol), TiCl$_3$ (30% in 2 N HCl$_{(aq)}$) (4.4 mL, 11.2 mmol), and ethanol (16 mL) were dissolved in a 100-mL round-bottom flask at room temperature and then cooled to 0° C. Compound 3 (1.01 g, 3.2 mmol) was added slowly within 30 minutes and the resultant mixture was stirred for one hour, followed by addition of $^t$BuNH$_2$.BH$_3$ (0.56 g, 6.4 mmol) within 20 minutes. After the resultant mixture was stirred for 6 hours at 0° C., it was cooled to room temperature and stirred for 14 hours. 3 N NaOH aqueous solution was added until pH>12 to stop reaction. The resultant mixture was concentrated to remove ethanol. Water phase was extracted with dichloromethane (3×30 mL) and then organic phase was collected, dried with anhydrous sodium sulfate, filtrated, and concentrated. The crude extract was purified by column chromatography (gradient elution, methanol:dichloromethane=1:10 to 1:5 as an eluent) to afford white solid compound 4 (0.66 g, 68%), white solid compound 2 (0.04 g, 4%), white solid compound 4a (0.11 g, 12%) and colorless liquid compound 4b (0.07 g, 15%).

Compound 4 is 2-exo-7,7-dimethyl-1-(morpholine-4-sulfonylmethyl)-bicyclo[2.2.1]hept-2-yl-amine, and its related properties are listed as follows:

Specific rotation: $[\alpha]_D^{24}$ −28.8 (c 1.0, CHCl$_3$).

$^1$H NMR (400 MHz, CDCl$_3$) δ 3.76 (t, J=4.8 Hz, 4H), 3.40 (d, J=13.2 Hz, 1H), 3.32-3.20 (m, 5H), 2.60 (d, J=13.2 Hz, 1H), 1.82-1.68 (m, 4H), 1.56 (br, 2H), 1.54-1.46 (m, 2H), 1.18-1.13 (m, 1H), 1.04 (s, 3H), 0.82 (s, 3H).

$^{13}$C NMR (100 MHz, CDCl$_3$) δ 66.5 (CH$_2$×2), 56.8 (CH), 49.2 (C), 48.8 (C), 45.8 (CH$_2$), 45.8 (CH$_2$×2), 44.6 (CH), 39.8 (CH$_2$), 32.2 (CH$_2$), 27.3 (CH$_2$), 21.1 (CH$_3$), 20.0 (CH$_3$).

IR (neat) 3427, 3395, 2954, 2921, 2863, 1455, 1339, 1325, 1260, 1148, 1114, 1075.

HRMS: calculated for C$_{14}$H$_{26}$N$_2$O$_3$S 302.1664. found 302.1681.

Compound 4a is 2-endo-7,7-dimethyl-1-(morpholine-4-sulfonylmethyl)-bicyclo[2.2.1]hept-2-ylamine, and its related properties are listed as follows:

Specific rotation: $[\alpha]_D^{24}$ +21.4 (c 1.1, CHCl$_3$).

$^1$H NMR (400 MHz, CDCl$_3$) δ 3.78-3.73 (m, 4H), 3.47-3.42 (m, 1H), 3.27-3.21 (m, 4H), 2.83 (d, J=13.6, 1H), 2.79 (d, J=13.6, 1H), 2.40-2.32 (m, 1H), 2.24-2.15 (m, 1H), 1.95 (br, 2H) 1.85-1.76 (m, 2H), 1.67-1.62 (m, 2H), 1.40-1.32 (m, 1H), 1.04 (s, 3H), 0.82 (s, 3H).

$^{13}$C NMR (100 MHz, CDCl$_3$) δ 66.4 (CH$_2$×2), 55.7 (CH), 51.7 (C), 51.7 (C), 50.1 (CH$_2$), 45.8 (CH$_2$×2), 44.0 (CH), 38.6 (CH$_2$), 28.1, (CH$_2$), 24.5 (CH$_2$), 20.4 (CH$_3$), 18.7 (CH$_3$).

IR (neat) 3399, 3335, 2937, 2872, 1456, 1340, 1259, 1154, 1110, 1075.

HRMS: calculated for C$_{14}$H$_{26}$N$_2$O$_3$S 302.1664. found 302.1647.

Compound 4b is 2,2-dimethyl-3-methylenecyclopentylacetonitrile, and its related properties are listed as follows:

Specific rotation: $[\alpha]_D^{24}$ +12.4 (c 1.3, CHCl$_3$).

$^1$H NMR (400 MHz, CDCl$_3$) δ 4.82 (t, J=2.4 Hz, 1H), 4.79 (t, J=2.4 Hz, 1H), 2.52-2.42 (m, 1H), 2.42-2.30 (m, 2H), 2.20-2.12 (m, 1H), 2.07-1.97 (m, 1H), 1.96-1.86 (m, 1H), 1.53-1.40 (m, 1H), 1.10 (s, 3H), 0.87 (s, 3H).

$^{13}$C NMR (100 MHz, CDCl$_3$) δ 159.7 (C), 119.5 (C), 104.6 (CH$_2$), 46.5 (CH), 43.8 (C), 29.8 (CH$_2$), 28.1 (CH$_2$), 26.9 (CH$_3$), 23.0 (CH$_3$), 17.9 (CH$_2$).

IR (neat) 3073, 3040, 2962, 2871, 2246, 1653, 1463, 1424, 1365.

HRMS: calculated for C$_{10}$H$_{15}$N 149.1205. found 149.1217.

(iv) Synthesis of Compound 5

Scheme 5d

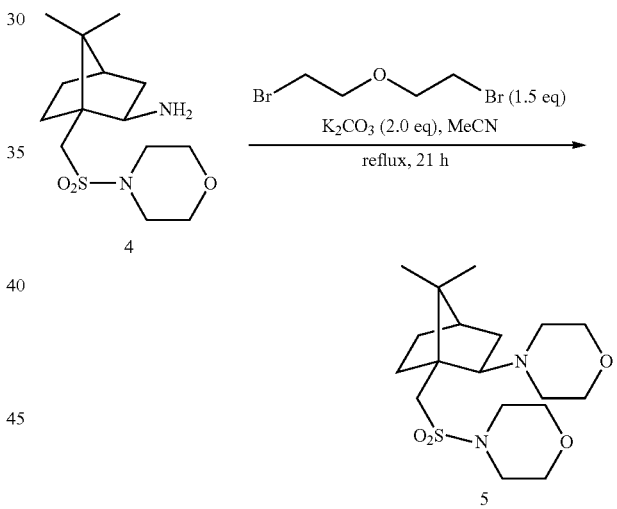

With reference to the Scheme 5d, compound 4 (0.66 g, 2.17 mmol), potassium carbonate (0.60 g, 4.34 mmol), C$_4$H$_8$Br$_2$O (0.41 mL, 3.25 mmol), and acetonitrile (10.8 mL) were refluxed for 21 hours in a 50-mL round-bottom flask, and then cooled to room temperature. The resultant mixture was concentrated to remove acetonitrile. Dichloromethane (10 mL) and deionized water (20 mL) were added, and water phase was further extracted with dichloromethane (3×20 mL). Organic phase was collected, dried with anhydrous sodium sulfate, filtrated, and concentrated. The crude extract was purified by column chromatography (gradient elution, methanol:dichloromethane=1:40 to 1:20 as an eluent) to afford white solid compound 5 (0.71 g, 87%), 4-(7,7-dimethyl-2-exo-morpholinyl-bicyclo[2.2.1]hept-1-ylmethanesulfonyl)-morpholine. The related properties of the compound 5 are listed as follows:

Specific rotation: $[\alpha]_D^{24}$ −33.6 (c 1.2, CHCl$_3$).

$^1$H NMR (400 MHz, CDCl$_3$) δ 3.76 (t, J=4.8 Hz, 4H), 3.70-3.57 (m, 5H), 3.30-3.17 (m, 4H), 2.76-2.65 (m, 2H), 2.64-2.50 (m, 4H), 2.18 (td, J=12.4 Hz, 4.8 Hz, 1H), 1.96-1.87 (m, 1H), 1.80-1.64 (m, 2H), 1.50-1.42 (m, 2H), 1.20-1.10 (m, 1H), 0.87 (s, 3H), 0.73 (s, 3H).

$^{13}$C NMR (100 MHz, CDCl$_3$) δ 71.0 (CH), 67.6 (CH$_2$×2), 66.4 (CH$_2$×2), 52.7 (CH$_2$×2), 49.4 (C), 48.6 (C), 45.7 (CH$_2$×2), 44.5 (CH$_2$), 43.9 (CH), 31.4 (CH$_2$), 31.1 (CH$_2$), 27.1 (CH$_2$), 20.9 (CH$_3$), 19.4 (CH$_3$).

IR (neat) 2954, 2886, 2853, 1455, 1344, 1328, 1261, 1154, 1115, 1074.

HRMS: calculated for C$_{18}$H$_{32}$N$_2$O$_4$S 372.2083. found 372.2075.

(v) Synthesis of (−)-MITH

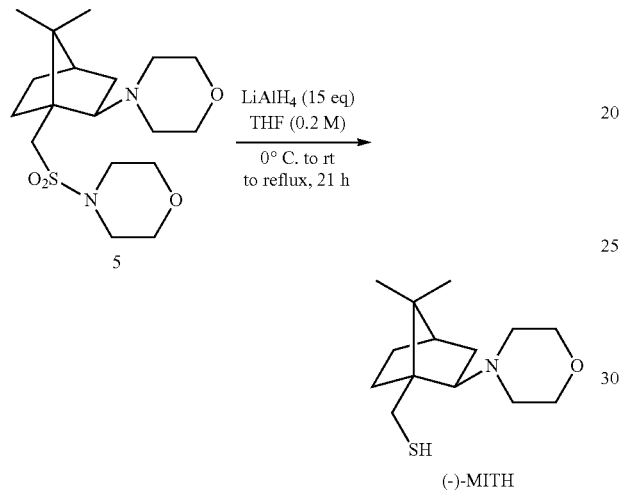

With reference to the Scheme 5e, to LiAlH$_4$ (0.80 g, 21.1 mmol) in a 25-mL round-bottom flask, THF (6.7 mL) was added under ice bath and compound 5 (0.50 g, 1.34 mmol) was further added. After the temperature of the mixture slowly goes back to ambient temperature, the mixture was refluxed for 21 hours. After the temperature of the mixture goes back to ambient temperature, ether (5 mL) was added to the mixture for dilution. Then, deionized water (0.8 mL), 3 N NaOH aqueous solution (0.8 mL), and deionized water (3.2 mL) were slowly added dropwise in sequence to stop reaction. The resultant mixture was stirred until its color changed from gray to white, and then filtrated with diatomite. The filtrate was collected and concentrated. The resultant solids were refluxed in dichloromethane for 5 minutes and then filtrated with diatomite, and this step was repeated three times. The concentrated crude extract was purified by column chromatography (ethyl acetate:n-hexane=1:20 as an eluent) to afford colorless oil (−)-MITH (0.16 g, 46%). The related properties of (−)-MITH are listed as follows:

Specific rotation: [α]$_D^{24}$ −79.8 (c 0.9, CHCl$_3$).

$^1$H NMR (400 MHz, CDCl$_3$): δ 3.68 (ddd, J=10.6 Hz, 6.4 Hz, 3.6 Hz, 2H), 3.62 (ddd, J=10.8 Hz, 6.4 Hz, 3.6 Hz, 2H), 2.84 (dd, J=13.2 Hz, 8.0 Hz, 1H), 2.70-2.50 (m, 4H), 2.42 (dd, J=9.2 Hz, 6.0 Hz, 1H), 1.94-1.84 (m, 1H), 1.74-1.62 (m, 2H), 1.58 (m, 3H), 1.42-1.26 (m, 2H), 1.12-1.05 (m, 1H), 0.88 (s, 3H), 0.83 (s, 3H).

$^{13}$C NMR (100 MHz, CDCl$_3$): δ 70.7 (CH), 67.6 (CH$_2$), 53.4 (C), 53.2 (CH$_2$), 48.0 (C), 45.7 (CH), 34.3, (CH$_2$), 31.8 (CH$_2$), 26.8 (CH$_2$), 23.7 (CH$_2$), 21.3 (CH$_3$), 19.8 (CH$_3$).

IR (neat) 2949, 2881, 2853, 2559, 1450, 1386, 1307 cm$^{-1}$.

Although synthesis of (−)-MITH is exemplified only, (+)-2-endo-morpholinoisobornane-10-thiol ((+)-MITH) can also been synthesized according to Schemes 5d and 5e if compound 4 is replaced by compound 4a as a staring material.

When (+)-MITH is used as a catalyst for enantioselective reaction, resultant products are enantiomers of those synthesized under catalysis of (−)-MITH.

In conclusion, the present invention applies simplified steps and avoids dangerous steps. Thus, 2-morpholinoisobornane-10-thiol can be prepared in mass production and it is advantageous to application in industry.

Although the present invention has been explained in relation to its preferred embodiment, it is to be understood that many other possible modifications and variations can be made without departing from the scope of the invention as hereinafter claimed.

What is claimed is:

1. A method for preparing 2-morpholinoisobornane-10-thiol, comprising the following steps:

(a) providing a compound represented by formula (I),

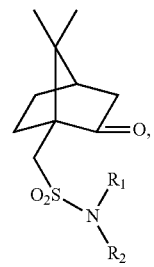

wherein each of R$_1$ and R$_2$, independently, is C$_{1-6}$ alkyl, C$_{5-10}$ cycloalkyl, C$_{4-9}$ heterocycloalkyl, C$_{6-10}$ aryl, or C$_{5-9}$ heteroaryl, and the heterocycloalkyl and the heteroaryl have at least one heteroatom selected from the group consisting of oxygen, sulfur, and nitrogen, or R$_1$ and R$_2$ together form —(CH$_2$)$_x$Z(CH$_2$)$_y$—, wherein x and y is 1, 2, or 3, and Z is CH$_2$, NH, O, or S;

(b) converting the compound represented by formula (I) into a compound represented by formula (II),

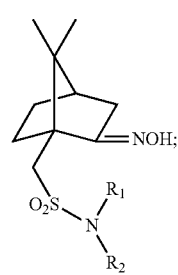

(c) reducing the compound represented by formula (II) into a compound represented by formula (III),

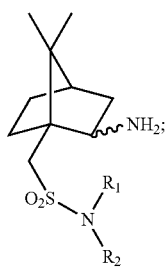

(d) forming a compound represented by formula (IV),

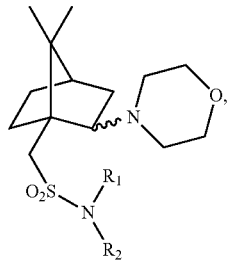

by N-alkylation of the compound represented by formula (III) with W$_1$—(CH$_2$)$_2$O(CH$_2$)$_2$—W$_2$, wherein W$_1$ and W$_2$ are leaving groups; and (e) reducing the compound represented by formula (IV) into 2-morpholinoisobornane-10-thiol.

2. The method as claimed in claim 1, wherein the compound represented by formula (I) in step (a) is formed by sulfamidation of (1S)-(+)-camphorsulfonic acid with a compound represented by formula (V),

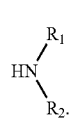

3. The method as claimed in claim 2, wherein the compound represented by formula (V) is morpholine.

4. The method as claimed in claim 1, wherein hydroxylamine is used as an iminating agent in step (b).

5. The method as claimed in claim 1, wherein t-BuNH$_2$·BH$_3$ is used as a reductant in step (c).

6. The method as claimed in claim 1, wherein the leaving groups in step (d) are halogen.

7. The method as claimed in claim 1, wherein LiAlH$_4$ is used as a reductant in step (e).

8. A method for preparing 2-morpholinoisobornane-10-thiol, comprising the following steps:

(a) providing a compound represented by formula (IV),

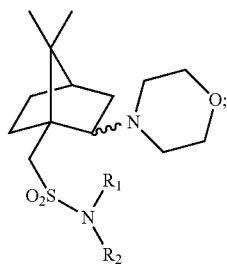

wherein each of R$_1$ and R$_2$, independently, is C$_{1-6}$ alkyl, C$_{5-10}$ cycloalkyl, C$_{4-9}$ heterocycloalkyl, C$_{6-10}$ aryl, or C$_{5-9}$ heteroaryl, and the heterocycloalkyl and the heteroaryl have at least one heteroatom selected from the group consisting of oxygen, sulfur, and nitrogen, or R$_1$ and R$_2$ together form —(CH$_2$)$_x$Z(CH$_2$)$_y$—, wherein x and y is 1, 2, or 3, and Z is CH$_2$, NH, O, or S; and (b) reducing the compound represented by formula (IV) into 2-morpholinoisobornane-10-thiol.

9. The method as claimed in claim 8, wherein LiAlH$_4$ is used as a reductant in step (b).

10. The method as claimed in claim 8, wherein the compound represented by formula (IV) is formed by N-alkylation of the compound represented by formula (III) with W$_1$—(CH$_2$)$_2$O(CH$_2$)$_2$—W$_2$,

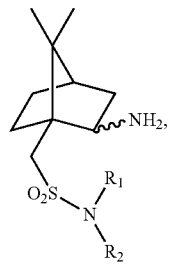

wherein W$_1$ and W$_2$ are leaving groups.

11. The method as claimed in claim 10, wherein the leaving groups are halogen.

12. The method as claimed in claim 10, wherein the compound represented by formula (III) is formed from imination reaction of a compound represented by formula (II),

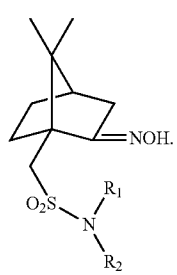

13. The method as claimed in claim 12, wherein t-BuNH$_2$·BH$_3$ is used as a reductant to reduce the compound represented by formula (II) into the compound represented by formula (III).

14. The method as claimed in claim 12, wherein the compound of formula (II) is formed by reduction of a compound represented by formula (I),

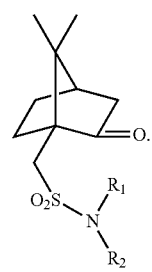

15. The method as claimed in claim 14, wherein hydroxylamine is used as an iminating agent to convert the compound represented by formula (I) into the compound represented by formula (II).

16. The method as claimed in claim 14, wherein the compound represented by formula (I) is formed by sulfamidation of (1S)-(+)-camphorsulfonic acid with a compound represented by formula (V),

17. The method as claimed in claim 16, wherein the compound represented by formula (V) is morpholine.

18. A compound represented by formula (VI):

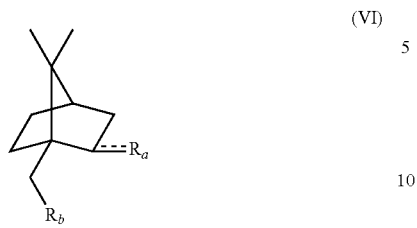
(VI)

wherein ═ is a single bond, $R_a$ is morpholino, and $R_b$ is

wherein each of $R_1$ and $R_2$, independently, is $C_{1-6}$ alkyl, $C_{5-10}$ cycloalkyl, $C_{4-9}$ heterocycloalkyl, $C_{6-10}$ aryl, or $C_{5-9}$ heteroaryl, and the heterocycloalkyl and the heteroaryl have at least one heteroatom selected from the group consisting of oxygen, sulfur, and nitrogen, or $R_1$ and $R_2$ together form —$(CH_2)_xZ(CH_2)_y$—, wherein x and y is 1, 2, or 3, and Z is $CH_2$, NH, O, or S.

19. The compound as claimed in claim 18, wherein x and y are 2 and Z is O.

* * * * *